United States Patent [19]

Young

[11] Patent Number: 4,461,729
[45] Date of Patent: * Jul. 24, 1984

[54] METHOD FOR THE SELECTIVE PREPARATION OF SECONDARY ALCOHOLS AND DERIVATIVES THEREOF

[75] Inventor: Lewis B. Young, Skillman, N.J.

[73] Assignee: Mobil Oil Corporation, New York, N.Y.

[*] Notice: The portion of the term of this patent subsequent to Dec. 21, 1999 has been disclaimed.

[21] Appl. No.: 410,288

[22] Filed: Aug. 23, 1982

Related U.S. Application Data

[63] Continuation-in-part of Ser. No. 222,835, Jan. 6, 1981, abandoned.

[51] Int. Cl.$^3$ ............... C07C 67/04; C07C 27/02; C07C 41/03
[52] U.S. Cl. ............... 260/459 R; 568/877; 568/618; 560/247; 260/980; 564/296; 252/351; 252/353; 252/357; 252/DIG. 1
[58] Field of Search ............... 560/247; 568/858, 877, 568/618; 260/459 R, 980; 564/296

[56] References Cited

U.S. PATENT DOCUMENTS

| | | | |
|---|---|---|---|
| 1,970,578 | 8/1934 | Schoeller et al. | 568/622 X |
| 2,671,116 | 3/1954 | Kosmin | 568/622 |
| 3,492,341 | 1/1970 | Trevillyan | 560/247 |
| 4,251,673 | 2/1981 | Mark et al. | 568/858 |
| 4,365,083 | 12/1982 | Young | 560/247 |
| 4,365,084 | 12/1982 | Young | 560/247 |

OTHER PUBLICATIONS

Brewster, Organic Chemistry, (1948), 228-229.
Morrison et al., Organic Chemistry, 3rd Ed., (1973), 455 and 752.
Schick, Nonionic Surfactants (1967), 384.
Kirk-Othmer Encyclopedia of Chemical Technology, Third Edition, vol. 1, pp. 728-729, (1978), Regarding the Conversion of Alcohols to Surfactants.

*Primary Examiner*—Bernard Helfin
*Attorney, Agent, or Firm*—A. J. McKillop; M. G. Gilman; E. F. Kenehan, Jr.

[57] ABSTRACT

A method for preparation of secondary alcohol mixtures by selective reaction of an olefin or olefin mixture and a carboxylic acid compound in the presence of a particular type of shape selective zeolite catalyst. The reaction selectively produces α-methylalkyl carboxylate enriched ester product which, upon subsequent hydrolysis, yields the desired 2-alcohol enriched secondary alcohol product.

15 Claims, No Drawings hydroxy alkyl compound with very little, if any, 3-hydroxy or higher structural isomer byproduct therein.

The particular type of shape-selective zeolite materials around which the process of the invention is constructed are characterized by their open crystal structure having channels or networks of pores which provide restricted passageways for entry and egress of the reactants. These zeolites may be identified by their characteristic Contraint Index of 1 to 12 and their relatively high silica to alumina ratios of at least 12. There are several known members of the class, such as zeolites ZSM-5, ZSM-11, ZSM-12, ZSM-23, ZSM-35, ZSM-38 and ZSM-48. Zeolite ZSM-12 is preferred.

In a preferred embodiment of the present invention, olefin mixtures are employed as the olefinic reactant in the first step of the process. Such mixture contains at least 25 mole percent of a $C_6$–$C_{20}$ olefin having no unsaturation at the site of the No. 2 carbon atom of the olefin.

DESCRIPTION OF SPECIFIC EMBODIMENTS

The subject of the present invention is a process for the manufacture of secondary alcohol mixtures having a high degree of hydroxy functionality at the 2-position of the hydrocarbon chain. Such mixtures are those which are enriched in alcohols represented by the formula:

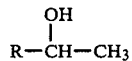

wherein R is alkyl of 1 to 18 carbon atoms. These types of alcohol mixtures, and surfactant chemicals based thereon, are found to have superior biodegradability as compared to similar compounds having random functional group points of attachment.

The first, and key, step in the process is the reaction of an olefin with a carboxylic acid compound to selectively produce an alkyl carboxylate ester product enriched in the α-methylalkyl carboxylate ester. The reaction is carried out under ester-forming conditions which include temperatures of between 25° C. and 600° C. and pressures within the approximate range of $10^4$ Pa to $10^7$ Pa (0.1–100 atm), although temperatures of 75° C. to 400° C. and pressures between $10^5$ Pa and $4 \times 10^6$ Pa are preferred. By utilization of the particular type of zeolite catalyst described hereinafter, it now becomes possible to react carboxylic acids with olefinic hydrocarbons having the carbon-carbon double bond in substantially any position in the molcule and to selectively produce an adduct wherein the carboxylate has attached principally at the #2 carbon of the olefin molecule.

The carboxylic acids useful in the process of the present invention are preferably alkyl carboxylic acids having from 1 to about 10 carbon atoms therein. Included within this group are formic acid, acetic acid, propionic acid, butyric acid and hexanoic acid. Slightly branched alkyl carboxylic acids are also useful, such as, for instance, isobutyric acid. Haloalkyl carboxylic acids, such as chloroacetic acid, fluoroacetic acid and trifluoroacetic acid may be employed. Also, aryl carboxylic acids will be found desirable in some instances, including benzoic acid, para-toluic acid and para-chlorobenzoic acid. For commercially viable applications it is expected that acetic acid will be found particularly desirable.

Olefins suitable for the selective production of α-methylalkyl carboxylate enriched mixtures as described herein are not limited to α-olefins. Rather, it has been found that substantially any olefinic hydrocarbon may be employed without regard to the location of the site of unsaturation. Mixed isomers of a given olefin are particularly desirable due to their ready availability and relatively low cost. Linear $C_3$ to $C_{20}$ olefins are especially preferred, but slightly branched olefins may also be employed. Some non-limiting illustrative examples would include: 1- and 2-pentenes, 1-, 2-, 3- and 4-octenes (or mixtures thereof), dodecenes, hexadecenes, 1-methylnonenes, 4-phenyl-1-butene, and so forth. Especially preferred olefinic reactants are olefin mixtures containing at least 25% of a $C_6$ to $C_{20}$ olefin having no unsaturation at the site of the No. 2 carbon atom thereof. It is especially surprising that olefins of this type can comprise a substantial part or even all of the olefinic reactant and still have the resulting alkyl carboxylate product enriched in the α-methylalkyl carboxylate.

The crystalline zeolites utilized herein are members of a particular class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this particular class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with silica to alumina mole ratios of at least 12 are useful, it is preferred in some instances to use zeolites having substantially higher silica/alumina ratios, e.g. 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also included within this definition are substan-

METHOD FOR THE SELECTIVE PREPARATION OF SECONDARY ALCOHOLS AND DERIVATIVES THEREOF

CROSS REFERENCE TO RELATED APPLICATION

This application is a continuation-in-part of the co-pending application of Lewis B. Young, said application having Ser. No. 222,835, filed Jan. 6, 1981 now abandoned.

BACKGROUND OF THE INVENTION

1. Field of the Invention

The invention disclosed herein is concerned with the preparation of secondary alcohol mixtures which are enriched in $C_3$–$C_{20}$ alkanols having hydroxy functionality in the 2-position. Such mixtures are prepared from olefinic compounds in the presence of carboxylic acids and particular zeolite catalysts.

2. Description of the Prior Art

Secondary alcohols can be prepared by hydrolysis of secondary alkyl carboxylate esters. The production of such alcohol precursors by reaction of carboxylic acids with olefins in the presence of Lewis Acid catalysts is known. However, the reaction results in the apparently indiscriminate addition of the carboxylate to either end of the olefin double bond, thereby giving rise to a mixture of structural isomers of the alkylcarboxylate product. Mineral acids (e.g. $H_2SO_4$) are also reported to catalyze the reaction, but the result is much the same, i.e. non-selective addition of the carboxylic acid to either side of the carbon-carbon double bond. Trevillyan; U.S. Pat. No. 3,492,341; Issued Jan. 27, 1970 discloses preparation of alkyl carboxylate esters by reacting carboxylic acids with 1- or 2-monoolefins over a mordenite zeolite catalyst.

Prior to the present invention the only known method for producing commercially valuable secondary alcohol mixtures enriched in alcohols having the hydroxy group in the 2-position has been to utilize substantially pure, but expensive, alpha-olefins as the starting material. Reaction of carboxylic acids with internal or mixed olefins using the common acid catalysts necessitated physical separation of the isomeric and structural variants of the alkyl carboxylic product (e.g. by distillation) in order to isolate the desired α-methylalkyl carboxylate alcohol precursor. Subsequent hydrolysis of the α-methylalkylcarboxylates in the product resulted in almost stoichiometric conversion to the 2-alcohol.

The resulting secondary alcohols can be converted into nonionic detergents by reaction with ethylene oxide. It has been shown that detergents of this type which contain a high degree of hydroxy functionality in the 2-position, are superior in biodegradability to comparable ethoxylates having random hydroxy functional attachment up and down the carbon chain.

Detergent range higher alcohols and their derivatives are used in a wide variety of industrial and consumer products. In general, these materials are used either for their surface-active properties, or as a means of introducing a long chain moiety into a chemical compound. Only a small amount of detergent range alcohol is used as is, but rather most of it is used as derivatives such as poly(oxyalkylene) ethers, or esters of acids such as sulfuric acid, phosphoric acid, and mono- and dicarboxylic acids.

Surfactants derived from detergent range alcohols are widely used where emulsifying, dispersing, wetting, or detergent properties are desired. These surfactants are readily biodegradable and are finding increased use in low phosphate and nonphosphate detergents. The alcohols provide the starting material for all of the surfactant types: nonionics, anionics, cationics and zwitterionics. The alkyl sulfates, such as sodium dodecyl sulfate, $C_{12}H_{25}OSO_3Na$, are known for their cleaning ability and voluminous, stable foam. Alkyl sulfates derived from $C_{12}$ through $C_{15}$ linear alcohols are widely used in consumer products, for instance in toothpastes, hair shampoos, carpet shampoos, and light-duty household cleaners, whereas those derived from $C_{16}$ and $C_{18}$ linear alcohols are used in heavy-duty household detergents. Detergents having good foam stability have been reported from mixtures of $C_{14}$, $C_{16}$, and $C_{18}$ linear alcohols. Minor amounts of unsulfated alcohol left in the alkyl sulfate detergents serve as foam stabilizers. The polyethoxylated alcohols, when sulfated and neutralized with a base such as sodium or ammonium hydroxide to give anionic surfactants, have wide application as light-duty dishwashing detergents and as part of the surfactant system of heavy-duty household liquid and granular detergents. These and other more specialized surfactants have a wide variety of industrial and household applications.

Cationic quaternary nitrogen surfactants of various types may be made by the condensation of tertiary amines with long chain alkyl halides, which are in turn obtained from the halogenation of a higher alcohol. Besides their use as surfactants, quaternary derivatives are widely used as disinfectants, bactericides, fungicides, antistatic agents, and textile softeners. Specialty phosphate ester surfactants and emulsifying agents are made by the reaction of phosphorous pentoxide and a detergent range alcohol. Other surfactants derived from these alcohols are alkyl amine oxides and alkyl glycerol sulfonates.

In another example of a surfactant application, dodecanol is used as a stabilizer for fire extinguishing foams. Hexadecanol and octadecanol are used in bar soaps and as antifoam agents in paper making and wastewater treatment, and dodecanol or higher alcohols are used to limit foaming in detergent compositions. The emulsion polymerization of various monomers is practiced in the presence of an alkyl sulfate surfactant, sometimes combined with free alcohol.

SUMMARY OF THE INVENTION

A method has now been found whereby substantially any linear olefinic compound, especially including mixtures of olefinic compounds, regardless of the position of the carbon-carbon double bond in the hydrocarbon chain, may be converted to secondary alcohol mixtures enriched in alcohols having hydroxy functionality in the 2-position. The conversion is accomplished by reaction under ester-forming conditions of the olefin or olefin mixtures with a $C_1$ to $C_{10}$ carboxylic acid compound, in the presence of a particular type of shape-selective zeolite catalyst, to selectively produce an alkyl carboxylate ester product enriched in α-methylalkyl carboxylate. The carboxylate ester product can then be hydrolyzed under hydrolysis conditions to yield the corresponding alcohol mixture enriched in the 2-

ZSM-5 is described in greater detail in U.S. Pat. Nos. 3,702,886 and Re 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 is more particularly described in European Patent Application No. 80 300,463, published Sept. 3, 1980 as Publication No. 0015132, the content of which is incorporated herein by reference.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 and ZSM-12 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. The high density must necessarily be associated with a relatively small amount of free space within the crystal, which might be expected to result in more stabile structures. This free space, however, is important as the locus of catalytic activity.

Crystal framework densities of some typical zeolites, including some which are not within the purview of this invention, are:

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 | tially pure silica analogs of the useful zeolites described herein, that is to say those zeolites having no measurable amount of aluminum (silica to alumina mole ratio of infinity) but which otherwise embody the characteristics disclosed.

The special class of zeolites, after activation, acquire an intracrystalline sorption capacity for normal hexane which is greater than that for water, i.e. they exhibit "hydrophobic" properties. This hydrophobic character can be used to advantage in some applications.

The particular class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48, and other similar materials.

2-position comprises at least 50% or even at least 60% of the total alcohol product.

In one embodiment of the invention, the secondary alcohols prepared as taught above are subsequently converted to a surfactant material having a high degree of functionality in the 2-position of the alkyl chain. Such surfactants are particularly desirable in applications wherein there is a likelihood that some or all of it may eventually find its way into the natural environment. While surfactants derived from detergent range alcohols are known to be generally biodegradable, it is also known that compounds exhibiting a high degree of 2-functionality are significantly superior to similar compounds having random functional group attachment in terms of biodegradability. The method of the present invention provides a relatively inexpensive way to obtain those very desirable 2-functional surfactants from a readily available mixed olefin starting material.

The surfactant derivatives of the secondary alcohols produced as provided above may be any of usual surfactant types: nonionic, anionic, cationic or zwitterionic. The techniques for preparing these types of surfactants are straight forward and well known to those conversant in the art. Generic teachings and/or discussions on the subject of preparing surfactant compounds from organic alcohols are to be found in the literature, such as, for example, the text entitled SURFACE ACTIVE AGENTS, THEIR CHEMISTRY AND TECHNOLOGY, Vol. 1, pp 202–205, by A. M. Schwartz and J. W. Perry (Interscience Publishers, Inc., 1949). Non-ionic detergents, for example, may be prepared by reaction of an alcohol with ethylene oxide or propylene oxide to introduce ether groups into the molecule to increase the hydrophilic character of the compound. The reaction is carried out under moderate conditions of temperature and pressure in the presence of alkaline catalysts. The number of ether groups necessary to effect complete water solubility depends, of course, on the molecular weight and structure of the hydrophobic portion of the molecule.

A particularly preferred embodiment of the invention contemplates conversion of the 2-alcohol enriched product, prepared as disclosed herein, to a nonionic detergent such as that derived from reaction of ethylene oxide with linear secondary alcohols.

Another embodiment contemplates the utilization of the 2-alcohol enriched product, prepared as described herein (e.g. 2-octanol), as a component of a phthalate plasticizer (i.e. dioctylphthalate) used to modify the properties of polymers.

The following examples are provided to illustrate the process of this invention, and particularly the critical first step, to aid those in the art in the understanding and practice thereof.

EXAMPLE 1

A mixture of linear octenes, containing 25% each of 1-octene, trans-2-octene, trans-3-octene and trans-4-octene, was reacted with excess acetic acid in the presence of HZSM-12 zeolite. The reaction was carried out in a stirred autoclave at 150° C.–200° C. and pressures of between 140 and 185 psig. The reaction mix consisted of 100 ml of an 8/1 molar combination of acetic acid and the mixed octenes and 1.0 g of the HZSM-12 zeolite. Samples were taken periodically and analyzed to follow the course of the reaction. The results are summarized in Table I.

TABLE I

REACTION OF MIXED OCTENES WITH ACETIC ACID OVER HZSM-12

| Reaction Time | Temperature | Pressure | Yield of $C_8OAc$ | $C_8H_{17}OAc$ Isomer Distribution | | |
|---|---|---|---|---|---|---|
| | | | | 2 | 3 | 4 |
| 0.5 hr | 150° C. | 155 psig | 10.5 wt % | 88% | 11% | 1% |
| 1.0 hr | 150° C. | 150 psig | 12.8 wt % | 87% | 12% | 1% |
| 2.75 hr | 150° C. | 140 psig | 17.0 wt % | 86% | 13% | 1% |
| 3.7 hr | 200° C. | 185 psig | 22.5 wt % | 78% | 20% | 2% |
| 5.7 hr | 200° C. | 170 psig | 24.6 wt % | 70% | 27% | 3% |

EXAMPLE 2

The reaction was repeated in the presence of $BF_3 \cdot Et_2O$, a conventional Lewis Acid Catalyst, at about 90° C. After 18.4 hours the yield of octylacetate was 21.8 wt %, representing about 15 mole % conversion of the octene. The octylacetate product contained the 2-/3-/4-octyl acetate isomers in the ratio of 49%/27%/24%, respectively.

In contrast, the ZSM-12 catalyzed reaction of Example 1 provided an isomer ratio of 78%/20%/2% at about 16 mole % conversion. This clearly demonstrates that alkylcarboxylates can be prepared with surprisingly high yield of 2-carbon attachment from mixed olefins by carrying out the reaction in the presence of ZSM-12 zeolite.

EXAMPLE 3

One gram of HZSM-12 zeolite ($SiO_2/Al_2O_3$ mole ratio 70) was placed in a 300 cc stainless steel autoclave equipped with a magnetically driven stirrer. The catalyst had been ground to a powder and calcined prior to use. Added 100 ml of a mixture of acetic acid and 1-octene (molar ratio=4/1) and heated to temperature. Samples were withdrawn periodically through a dip tube and analyzed. Results are summarized in TABLE II.

TABLE II

REACTION OF 1-OCTENE AND ACETIC ACID OVER HZSM-12

| Reaction Time | Temperature | Pressure | Yield of $C_8OAc$ | $C_8H_{17}OAc$ Isomer Distribution | | |
|---|---|---|---|---|---|---|
| | | | | 2 | 3 | 4 |
| 3.5 hr | 150° C. | 160 psig | 5.9 wt % | 96.9% | 2.9% | 0.2% |
| 5.6 hr | 200° C. | 240 psig | 23.9 wt % | 94.1% | 5.5% | 0.4% |
| 73.2 hr | 200° C. | 230 psig | 32.2 wt % | 91.4% | 8.1% | 0.5% |

The 1-octene and acetic acid have been converted to primarily 2-octyl acetate. The 3- and 4-octyl acetates were produced as minor byproducts and no 1-octyl acetate was formed.

EXAMPLE 4

2-Octene and acetic acid were reacted in the same manner as in Example 3. The catalyst was another sample of the same HZSM-12 zeolite and the 2-octene reactant was a mixture of the cis and trans isomers. The results are shown in TABLE III.

TABLE III

REACTION OF 2-OCTENE AND ACETIC ACID OVER HZSM-12

| Reaction Time | Temperature | Pressure | Yield of $C_8OAc$ | $C_8H_{17}OAc$ Isomer Distribution | | |
|---|---|---|---|---|---|---|
| | | | | 2 | 3 | 4 |
| 0.8 hr | 150° C. | 175 psig | 0.4 wt % | 77% | 23% | — |

|  | Void Volume | Framework Density |
|---|---|---|
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 50% by weight of the original alkali metal contained in the zeolite as-synthesized, usually 0.5% by weight or less. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing the alkyl carboxylate-forming step of the present process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in some processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

An especially useful modifying treatment entails steaming of the zeolite by contact with an atmosphere containing from about 5 to about 100 percent steam at a temperature of from about 250° C. to about 1000° C. Steaming may last for a period of between about 0.25 and about 100 hours and may be conducted at pressures ranging from sub-atmospheric to several hundred atmospheres to reduce the alpha value of the zeolite to less than 500, and preferably less than 20, but greater than zero.

The carboxylate ester forming step of the process described herein may be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The latter, after use, can be conducted to a regeneration zone where coke is burned from the catalyst in an oxygen-containing atmosphere (such as air) at elevated temperature, after which the regenerated catalyst is recycled to the conversion zone for further contact with the organic reactants.

As indicated, the alkyl carboxylate reaction product is enriched in the α-methylalkyl carboxylate isomer. For purposes of the present invention, the alkyl carboxylate product is enriched in α-methalkyl carboxylate when the α-methylalkyl isomer comprises at least 40% of the total alkyl carboxylate product. Preferably the α-methylalkyl isomer comprises at least 50% or even at least 60% of the total alkyl carboxylate product.

The α-methylalkyl enriched carboxylate ester product of the first step of the process can then be hydrolyzed under hydrolysis conditions to convert the ester functionality to the corresponding secondary alcohol. The hydrolysis of esters is well known in the chemical literature and may be carried out in any of a number of ways.

In general, the reaction is normally carried out in basic medium wherein the ester is cleaved to produce the salt of the corresponding carboxylic acid and to hydrolyze the methylalkyl moiety to the alcohol, with the —OH function replacing the ester at the same point of attachment to the carbon chain. The reaction is straightforward and substantially quantitative, with no migration of the point of attachment, so that the α-methylalkyl-enriched carboxylate product is converted substantially entirely to the secondary alcohol. The salt of the carboxylic acid may be recovered and hydrolyzed back to the acid for subsequent recycling for further reaction with olefins as discussed hereinabove.

A preferred method of hydrolyzing the ester product contemplates refluxing with aqueous sodium or potassium hydroxide solution. The alkaline mixture is thereafter distilled to recover the alcohol. If necessary, the distillate may be saturated with sodium or potassium carbonate to liberate the alcohol—i.e., separate it from the aqueous component of the distillate.

The hydrolysis reaction may be carried out on the entire product mixture of the foregoing carboxylation reaction step or, alternatively, the α-methylalkyl-enriched carboxylate may be separated from some or all of the other components of the carboxylation reaction product mixture. In either event, the hydrolysis reaction product is subsequently separated by conventional means, such as fractional distillation, to recover an alcohol fraction enriched in the desired secondary alcohol isomer having hydroxy functionality at the 2-position. As with the alkyl carboxylate product of the initial process step, the alcohol product is enriched in alcohols having hydroxy functionality at the 2-position for purposes of this invention if this 2-isomer comprises at least 40% of the total alcohol product. Again preferably the secondary alcohol having hydroxy functionality in the

TABLE VIII-continued

REACTION OF 4-OCTENE AND ACETIC ACID

| Reaction Time | Temperature | Pressure | Yield of C$_8$OAc | C$_8$H$_{17}$OAc Isomer Distribution | | |
|---|---|---|---|---|---|---|
| | | | | 2 | 3 | 4 |
| 2.1 hr | 250° C. | 375 psig | 7.1 wt % | 4% | 10% | 86% |
| 3.6 hr | 250° C. | 390 psig | 11.5 wt % | 10% | 17% | 73% |

TABLE IX

CATALYST COMPARISONS

| Catalyst | 2-C$_8$OAc | 3-C$_8$OAc | 4-C$_8$OAc | Ratio: 2C$_8$OAc / 3 + 4-C$_8$OAc |
|---|---|---|---|---|
| HZSM-12 | 60% | 30% | 10% | 1.50 |
| BF$_3$ Et$_2$O | 8% | 18% | 75% | 0.09 |
| SiO$_2$/Al$_2$O$_3$ | 6% | 11% | 83% | 0.06 |
| REY | 10% | 17% | 73% | 0.11 |

As the comparisons of TABLE IX show, conventional catalysts and the large pore zeolite, REY, all result in the product arising from addition of the carboxylic acid to the double bond. HZSM-12, however, selectively yields 2-octyl acetate as the major product.

EXAMPLE 13

Using the same reaction method, 4-octene and propionic acid were reacted over 1.0 g of HZSM-12. The reaction mixture consisted of 100 ml of an 8:1 molar ratio mixture of the acid to the olefin. The results are shown in TABLE X.

TABLE X

REACTION OF 4-OCTENE AND PROPIONIC ACID OVER HZSM-12

| Reaction Time | Temperature | Pressure | C$_8$H$_{17}$OAc Isomer Distribution | | |
|---|---|---|---|---|---|
| | | | 2 | 3 | 4 |
| 1.0 hr | 150° C. | 150 psig | 62% | 16% | 22% |
| 2.4 hr | 200° C. | 195 psig | 59% | 21% | 20% |

EXAMPLE 14

Isobutyric acid and t-4-octene (molar ratio=6.2:1) were reacted over HZSM-12 zeolite. The results are summarized below.

TABLE XI

REACTION OF 4-OCTENE AND ISOBUTYRIC ACID OVER HZSM-12

| Reaction Time | Temperature | Pressure | Yield of C$_8$OBu | C$_8$H$_{17}$OAc Isomer Distribution | | |
|---|---|---|---|---|---|---|
| | | | | 2 | 3 | 4 |
| 3.1 hr | 200° C. | 200 psig | 3.8 wt % | 67% | 21% | 12% |
| 4.0 hr | 250° C. | 275 psig | 7.0 wt % | 50% | 32% | 18% |

EXAMPLE 15

To illustrate reaction of a cycloolefin in the process, a mixture of norbornene (bicyclo[2.2.1]-2-heptene) and acetic acid was reacted over HZSM-12 zeolite. The reaction was carried out on a steam bath at about 100° C. for 5.5 hours. The addition product, norbornyl acetate, was formed in about 95% yield.

EXAMPLE 16

Propylene was reacted with acetic acid in the presence of HZSM-12. Into a 300 cc autoclave were placed 70 ml of glacial acetic acid and 1.0 g of the HZSM-12 zeolite. The reactor was heated to 200° C. and liquid propylene was added at the rate of 10 ml per hour. Samples were periodically withdrawn and analyzed. The results are summarized in TABLE XII. As will be seen from the table, isopropyl acetate was formed in high yield with high purity.

TABLE XII

REACTION OF PROPYLENE WITH ACETIC ACID

| Reaction | Temperature | Pressure | Yield of isopropyl acetate | Yield of n-propyl acetate | Isopropyl acetate % of theory |
|---|---|---|---|---|---|
| 0.5 hr | 200° C. | 160 psig | 2.9 wt % | — | 36% |
| 1.5 hr | 200° C. | 240 psig | 8.0 wt % | — | 34% |
| 2.5 hr | 200° C. | 340 psig | 12.8 wt % | — | 36% |
| 3.5 hr | 200° C. | 450 psig | 17.0 wt % | — | 36% |
| 4.5 hr | 200° C. | 550 psig | 20.5 wt % | — | 35% |
| 20.9 hr | 200° C. | 400 psig | 31.6 wt % | 0.03 wt % | 50% |

Subsequent hydrolysis of the α-methylalkyl carboxylate containing products of these examples by conventional hydrolysis techniques will be substantially quantitative. Further, the reaction causes very little, if any isomerization of the alkylate so that the α-methylalkyl enriched carboxylate is converted substantially in its entirety to the desired 2-alcohol enriched alcohol product.

Although the foregoing will illustrate certain preferred embodiments of the process of my invention, it is of course to be understood that numerous variations thereon may be made without departing from the spirit and scope of the invention. Such being the case, there should be no undue limitation implied except as expressly set forth by the following claims.

What is claimed is:

1. A process for the preparation of secondary alcohol mixtures enriched in alcohols of the formula

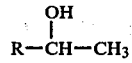

wherein R is alkyl of 1 to 18 carbon atoms, said process comprising (A) reacting an olefin mixture containing at least 25 percent of a C$_6$ to C$_{20}$ olefin having no unsaturation at the site of the No. 2 carbon atom thereof, with a C$_1$ to C$_{10}$ carboxylic acid, said reaction being carried out under ester-forming reaction conditions including the presence of a catalyst comprising crystalline zeolite material having a silica to alumina mole ratio of at least 12 and a Constraint Index of from about 1 to 12, to thereby selectively produce an alkyl carboxylate ester product which is enriched in the α-methylalkyl carboxylate ester; and (B) subsequently hydrolyzing said α-methylalkyl carboxylate-enriched ester product under hydrolysis reaction conditions, to thereby provide said secondary alcohol mixture enriched in alcohols having hydroxy functionality at the 2-position.

2. The process of claim 1 wherein said ester-forming reaction conditions include a temperature of between about 25° C. and 600° C. and a pressure of within the range of 10$^4$ Pa to 10$^7$ Pa.

3. The process of claim 1 wherein said carboxylic acid is selected from acetic acid, propionic acid and butyric acid.

TABLE III-continued
REACTION OF 2-OCTENE AND ACETIC ACID OVER HZSM-12

| Reaction Time | Temperature | Pressure | Yield of C$_8$OAc | C$_8$H$_{17}$OAc Isomer Distribution 2 | 3 | 4 |
|---|---|---|---|---|---|---|
| 1.4 hr | 200° C. | 245 psig | 6.9 wt % | 79% | 19% | 1.7% |
| 2.3 hr | 200° C. | 245 psig | 12.9 wt % | 79% | 20% | 0.6% |
| 3.3 hr | 200° C. | 235 psig | 18.3 wt % | 78% | 22% | 0.7% |
| 4.3 hr | 225° C. | 300 psig | 22.0 wt % | 75% | 24% | 1.0% |
| 6.3 hr | 225° C. | 300 psig | 24.1 wt % | 69% | 28% | 2.2% |

The use of HZSM-12 zeolite to promote the reaction is seen to significantly alter the isomeric product distribution from that which would normally be expected. Using the same reactor system and procedure, comparative runs were made with other catalysts as follows:

EXAMPLE 5

2-Octene and acetic acid were reacted over 1.0 g of HZSM-5 zeolite. The conditions of reaction were the same as in Example 4 and the results are summarized in TABLE IV.

TABLE IV
REACTION OF 2-OCTENE AND ACETIC ACID OVER HZSM-5

| Reaction Time | Temperature | Pressure | Yield of C$_8$OAc | C$_8$H$_{17}$OAc Isomer Distribution 2 | 3 | 4 |
|---|---|---|---|---|---|---|
| 2.0 hr | 200° C. | 290 psig | 3.6 wt % | 80% | 17% | 3% |
| 2.8 hr | 250° C. | 460 psig | 9.0 wt % | 70% | 23% | 7% |
| 4.0 hr | 250° C. | 445 psig | 10.4 wt % | 55% | 30% | 16% |
| 6.1 hr | 250° C. | 440 psig | 13.0 wt % | 46% | 32% | 23% |

EXAMPLE 6

Amorphous silica-alumina: SiO$_2$/Al$_2$O$_3$=90/10.

EXAMPLE 7

Zeolite REY.

EXAMPLE 8

A Lewis Acid catalyst: BF$_3$ Et$_2$O

A mixture of acetic acid and 2-octene (molar ratio 4:1, respectively) was mixed with a small amount of boron trifluoride ethereate catalyst and the mixture heated to 90° C. on a steam bath. Samples were removed and analyzed at 1.2 and 2.7 hours.

The reactions of Examples 6-8 are summarized in TABLE V and a comparison with the HZSM-5 and HZSM-12 zeolite is presented in TABLE VI.

TABLE V
REACTION OF 2-OCTENE AND ACETIC ACID

| Reaction Time | Temperature | Pressure | Yield of C$_8$OAc | C$_8$H$_{17}$OAc Isomer Distribution 2 | 3 | 4 |
|---|---|---|---|---|---|---|
| Catalyst: BF$_3$ Et$_2$O | | | | | | |
| 1.2 hr | 90° C. | 0 psig | 37.3 wt % | 52% | 45% | 3% |
| 2.7 hr | 90° C. | 0 psig | 57.0 wt % | 52% | 44% | 4% |
| Catalyst: amorphous SiO$_2$/Al$_2$O$_3$ | | | | | | |
| 0.6 hr | 250° C. | 400 psig | 5.0 wt % | 58% | 37% | 5% |
| 1.8 hr | 250° C. | 400 psig | 11.1 wt % | 59% | 36% | 5% |
| 17.5 hr | 250° C. | 400 psig | 17.4 wt % | 62% | 30% | 8% |
| Catalyst: REY | | | | | | |
| 2.2 hr | 200° C. | 215 psig | 1.9 wt % | 59% | 37% | 4% |
| 3.2 hr | 250° C. | 380 psig | 9.5 wt % | 60% | 35% | 5% |
| 3.9 hr | 250° C. | 380 psig | 14.5 wt % | 59% | 34% | 6% |
| 5.0 hr | 250° C. | 375 psig | 16.6 wt % | 59% | 31% | 10% |

TABLE VI
CATALYST COMPARISONS

| Catalyst | 2-C$_8$OAc | 3-C$_8$OAc | 4-C$_8$OAc | Ratio: 2C$_8$OAc / (3 + 4-C$_8$OAc) |
|---|---|---|---|---|
| HZSM-5 | 80% | 17% | 3% | 4.0 |
| HZSM-12 | 79% | 20% | 0.6% | 3.4 |
| BF$_3$.Et$_2$O | 52% | 44% | 4% | 1.1 |
| SiO$_2$/Al$_2$O$_3$ | 62% | 30% | 8% | 1.6 |
| REY | 60% | 35% | 5% | 1.5 |

It will be clearly seen from the data that the proportion of 2-isomer produced is significantly improved by utilization of HZSM-5 and HZSM-12 zeolites to catalyze the reaction. Similar improvement can be expected from the other zeolites encompassed within the herein described class.

EXAMPLE 9

To demonstrate even more dramatically the novel selectivity of the herein disclosed process, an olefin having the double bond in a more internal location—i.e., trans-4-octene—was reacted with acetic acid in the presence of HZSM-12. The reaction mixture contained a 10/1 molar ratio of HOAc to trans-4-octene. The results are given in TABLE VII.

TABLE VII
REACTION OF 4-OCTENE AND ACETIC ACID OVER HZSM-12

| Reaction Time | Temperature | Pressure | Yield of C$_8$OAc | C$_8$H$_{17}$OAc Isomer Distribution 2 | 3 | 4 |
|---|---|---|---|---|---|---|
| 1.3 hr | 150° C. | 170 psig | 1.5 wt % | 61% | 24% | 15% |
| 2.1 hr | 200° C. | 225 psig | 10.5 wt % | 60% | 30% | 10% |
| 2.8 hr | 200° C. | 225 psig | 17.3 wt % | 58% | 32% | 10% |
| 3.6 hr | 200° C. | 225 psig | 24.3 wt % | 57% | 32% | 11% |
| 5.6 hr | 200° C. | 225 psig | 27.4 wt % | 54% | 33% | 12% |

EXAMPLES 10-12

Using the same reaction mixture as Example 9, comparative reactions were carried out with a Lewis acid catalyst (BF$_3$ Et$_2$O) as well with amorphous silica-alumina and zeolite REY. Results are shown in TABLE VIII. A direct comparison of the isomeric distribution of the octyl actate product with that resulting from ZSM-12 is provided in TABLE IX.

TABLE VIII
REACTION OF 4-OCTENE AND ACETIC ACID

| Reaction Time | Temperature | Pressure | Yield of C$_8$OAc | C$_8$H$_{17}$OAc Isomer Distribution 2 | 3 | 4 |
|---|---|---|---|---|---|---|
| Catalyst: BF$_3$ Et$_2$O | | | | | | |
| 0.6 hr | 90° C. | 0 psig | 9.0 wt % | 1% | 5% | 94% |
| 4.3 hr | 90° C. | 0 psig | 65.7 wt % | 8% | 18% | 75% |
| Catalyst: amorphous SiO$_2$/Al$_2$O$_3$ | | | | | | |
| 2.3 hr | 250° C. | 390 psig | 3.5 wt % | 5% | 10% | 85% |
| 3.5 hr | 250° C. | 390 psig | 6.9 wt % | 5% | 10% | 85% |
| 4.9 hr | 250° C. | 390 psig | 8.4 wt % | 6% | 11% | 83% |
| Catalyst: REY | | | | | | |
| 1.6 hr | 200° C. | 225 psig | 4.1 wt % | 4% | 7% | 89% |

4. The process of claim 1 wherein the olefins in said olefin mixture are linear or slightly branched and have from 3 to about 20 carbon atoms therein.

5. The process of claim 1, 2, 3 or 4 wherein said zeolite is selected from the group consisting of ZSM-5, ZSM-11, ZSM-12, ZSM-23, ZSM-35, ZSM-38 and ZSM-48.

6. The process of claim 5 wherein said zeolite is ZSM-5.

7. The process of claim 5 wherein said ZSM-5 additionally comprises a binder therefor.

8. The process of claim 5 wherein said zeolite is ZSM-12.

9. The process of claim 1 wherein said hydrolysis conditions include carrying out said hydrolysis in a basic medium.

10. The process of claim 9 wherein said basic medium comprises an aqueous solution of sodium hydroxide or of potassium hydroxide.

11. The process of claim 1 further comprising the step of converting said secondary alcohol mixture to a surface active agent, wherein said secondary alcohol mixture is converted to a nonionic detergent by reaction with ethylene oxide.

12. The process of claim 1 further comprising the step of converting said secondary alcohol mixture to a surface active agent, wherein said secondary alcohol mixture is sulfated.

13. The process of claim 1 further comprising the step of converting said secondary alcohol mixture to a surface active agent, wherein said secondary alcohol mixture is polyethoxylated, then sulfated and then neutralized with sodium hydroxide or ammonium hydroxide.

14. The process of claim 1 further comprising the step of converting said secondary alcohol mixture to a surface active agent, wherein said secondary alcohol mixture is halogenated and condensed with a tertiary amine to form a cationic quaternary nitrogen surfactant.

15. The process of claim 1 further comprising the step of converting said secondary alcohol mixture to a surface active agent, wherein said secondary alcohol mixture is reacted with phosphorus pentoxide to produce a phosphate ester surfactant.

* * * * *